(12) United States Patent
Carson et al.

(10) Patent No.: US 9,341,625 B2
(45) Date of Patent: May 17, 2016

(54) CELL-SURFACE SIGNATURES FOR ISOLATING NEURONS FROM CELL CULTURES DERIVED FROM PLURIPOTENT STEM CELLS

(71) Applicant: Becton, Dickinson and Company, Franklin Lakes, NJ (US)

(72) Inventors: Christian T. Carson, Del Mar, CA (US); Jody Martin, Encinitas, CA (US); Jason G. Vidal, Oceanside, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/381,547

(22) PCT Filed: Apr. 23, 2013

(86) PCT No.: PCT/US2013/037781
§ 371 (c)(1),
(2) Date: Aug. 27, 2014

(87) PCT Pub. No.: WO2013/173031
PCT Pub. Date: Nov. 21, 2013

(65) Prior Publication Data

US 2015/0050667 A1    Feb. 19, 2015

Related U.S. Application Data

(60) Provisional application No. 61/647,951, filed on May 16, 2012.

(51) Int. Cl.
*G01N 33/569* (2006.01)

(52) U.S. Cl.
CPC .... *G01N 33/56966* (2013.01); *G01N 33/56977* (2013.01); *G01N 2333/7055* (2013.01); *G01N 2333/70596* (2013.01); *G01N 2333/71* (2013.01)

(58) Field of Classification Search
CPC .................. G01N 33/56966; G01N 33/56977; G01N 2333/7055
See application file for complete search history.

(56) References Cited

U.S. PATENT DOCUMENTS

| | | | | |
|---|---|---|---|---|
| 2012/0156230 | A1* | 6/2012 | Abbot | A61K 35/50 424/184.1 |
| 2012/0219535 | A1* | 8/2012 | Maxson, Jr. | C12N 5/0623 424/93.7 |

FOREIGN PATENT DOCUMENTS

| | | |
|---|---|---|
| WO | 2007/114634 A1 | 10/2007 |
| WO | 2011041062 A1 | 4/2011 |

OTHER PUBLICATIONS

Wilson et al. Development and Differentiation of Neural Rossettes Derived from Human Embryonic Cells. Stem Cell Reviews (2): 67-77 (2006).*

(Continued)

*Primary Examiner* — Gail R Gabel
(74) *Attorney, Agent, or Firm* — Bret E. Field; Bozicevic, Field & Francis LLP

(57) ABSTRACT

The inventors disclose methods and systems that provide for the isolation and purification of neurons directly from heterogeneous cell cultures. The expression of various cell adhesion molecules was examined in pluripotent stem cells. Changes in the expression of one or more of these molecules correlates with the progression of cells from non-lineage committed to neural cells. Using one or more antibodies for these molecules in combination with antibodies specific for CD200 will enable one to identify and isolate neurons from a population cells.

14 Claims, 15 Drawing Sheets

(56) References Cited

OTHER PUBLICATIONS

Elkabetz et al. "Human ES cell-derived neural rosettes reveal a functionally distinct early neural stem cell stage", Genes & Development, vol. 22, pp. 152-165 (2008).

Germain et al. "Embryonic Stem Cell Neurogenesis and Neural Specification", Journal of Cellular Biochemistry, vol. 111, pp. 535-542 (2010).

Ohyama et al. "Characterization and isolation of stem cell-enriched human hair follicle bulge cells", The Journal of Clinical Investigation, vol. 116, No. 1, pp. 249-260 (Jan. 2006).

Sergent-Tanguy et al. "Cell surface antigens on rat neural progenitors and characterization of the CD3(+)/CD3(-) cell populations", Differentiation, vol. 74, pp. 530-541 (2006).

Vidal et al. "CD200 and HLA-A, B, C enables the isolation of neurons from neural induction cultures of human embryonic stem cells", ISSCR 2012 Annual Meeting, Yokohama, Japan (Jun. 13-16, 2012), 21 pages.

Walker et al. "Decreased expression of CD200 and CD200 receptor in Alzheimer's disease: A potential mechanism leading to chronic inflammation", Experimental Neurology, vol. 215, No. 1, pp. 5-19 (Jan. 2009).

Wilson et al. "Development and Differentiation of Neural Rosettes Derived from Human Embryonic Stem Cells", Stem Cell Reviews, vol. 2, pp. 67-77 (2006).

Yuan et al. "Cell-Surface Marker Signatures for the Isolation of Neural Stem Cells, Glia and Neurons Derived from Human Pluripotent Stem Cells", PLoS One, vol. 6, No. 3, Article No. e17540, pp. 1-16 (Mar. 2011).

\* cited by examiner

CELL-SURFACE SIGNATURES FOR ISOLATING NEURONS FROM CELL CULTURES DERIVED FROM PLURIPOTENT STEM CELLS

CROSS-REFERENCE TO RELATED APPLICATIONS

Pursuant to 35 U.S.C. §119 (e) this application claims priority to the filing date of U.S. Provisional Patent Application Ser. No. 61/647,951 filed May 16, 2012; the disclosure of which application is herein incorporated by reference.

FIELD OF THE INVENTION

This invention relates to methods and compositions for the isolation of neurons.

BACKGROUND OF THE INVENTION

Both human embryonic stem cells (hESC) and human induced pluripotent stem cells (hiPSC) have the ability to differentiate into somatic cells. Thus, hESC and hiPSC differentiation offers an opportunity for therapy development, drug screening, disease modeling, and tissue replacement. However, developing well-defined conditions to generate pure populations of specific cell types is critical to achieve these goals. There are several neural induction methods that induce cell cultures to form neural stem cells (NSC) using spontaneous differentiation, chemical induction or mouse stromal feeder cells. NSC may be manually isolated and propagated as monolayer cultures for many passages. In principle, these cells may differentiate to neurons and glia, providing an endless supply of cells for in vitro and in vivo assays. Unfortunately, the robustness of these methods is hampered by batch-to-batch variability of isolated NSC. Moreover, differentiation of NSC often results in variable and heterogeneous cultures of neurons, glia and undifferentiated cells, which may impede downstream applications that require purified or defined cell populations, such as in vitro assays, transplantation and micro arrays. One possible solution to this problem is to identify cell surface markers expressed on NSC, glia and neurons to define and purify distinct cell types.

Cell surface marker expression has been described for the identification and isolation of many neural cell types by fluorescence-activated cell sorting FACS from embryonic and adult tissue from multiple species. The glycoprotein CD133 is a known stem/progenitor cell marker in many tissues and has been used to isolate NSC from human brain. The carbohydrate moiety CD15, also known as stage-specific embryonic antigen-1 or LeX, has been used to isolate NSC and radial glia from the sub-ventricular zone (SVZ) in mice. CD184, a G protein coupled receptor, was successfully used in combination with CD15 to isolate NSC from mouse embryonic forebrain and adult SVZ. CD24 is a cell adhesion molecule that has been used to isolate NSC from mouse brain by FACS. In addition, neural stem cells and neural progenitors have been isolated from human brain tissue using genetic promoter-reporters of neural stem cell markers.

Likewise, advancements have been made in the identification and isolation of hESC-derived neural cells by FACS. Pruszak et al., (Stem Cells 25: 2257-2268, 2007) reported that cultures of hESC differentiating to neural lineages may be assayed at different developmental stages with cell surface markers and that neurons could be enriched using an antibody to CD56 (NCAM). CD 184$^+$/CD326$^-$ markers have been used to purify neural progenitors capable of differentiation into neurons from differentiating hESC. In addition, Peh et al. (Stem Cells Dev 18: 269-282, 2009) have reported the enrichment for neurosphere-forming NSC from neural induction cultures of hESC based on expression for CD133, CD15 and GCTM-2. Using a similar strategy, Golebiewska et al., (Stem Cells 27: 1298-1308, 2009) used CD133$^+$/CD45$^-$/CD340$^-$ to isolate NSC from differentiating hESC. Pruszak et al., (2009) demonstrated the utility of CD24, CD15 and CD29 as a surface maker code for isolating distinct cell populations, including NSC and a mixed population of neuroblasts and neurons from neural induction cultures of hESC.

Yuan et al., (PLoS One. 2011 Mar. 2; 6(3):e17540), incorporated herein by reference, describes methods based on cell surface signatures to isolate neural stem cells (NSC), neural differentiation cultures of pluripotent stem cells by FACS. The methods were used to isolate a population of NSC that was CD 184$^+$/CD271$^-$/CD44$^-$/CD24$^+$ from neural induction cultures of hESC and human induced pluripotent stem cells (hiPSC). Cell surface signature-based methods were also used to enrich NSC from multiple common neural induction culture systems. Yuan et al., further identified cell surface signatures for the isolation of neurons and glia from isolated cultures of isolated NSC cultures. A population of neurons that was CD184$^-$/CD44$^-$/CD15LOW/CD24$^+$ and a population of glia that was CD 184$^+$/CD44$^+$ were subsequently purified from isolated cultures of differentiating NSC. The BD Stemflow™ Neural Cell Isolation Kit (BD Biosciences, San Jose, Calif.) is a reagent kit designed to allow the isolation of neural stem cells (NSCs) derived from human pluripotent stem cells or the isolation of neurons and glial cells from differentiated NSCs. This method reduces the amount of variability between NSC isolations as opposed to traditional methods like manual isolation but require the induction and isolation of NSC before isolation and enrichment of neurons in a culture. Methods are needed that provide for the identification and isolation of neurons derived from heterogeneous cell population and reduce the steps involved in neuron identification, isolation and enrichment.

SUMMARY

The present invention provides cell-surface signatures, methods and systems for the isolation or enrichment of neurons from heterogeneous populations of cells. The methods may be used to identify neurons from the expression pattern of a novel set of cell-surface proteins (cell-surface signatures). The present methods enable the isolation or enrichment of neurons from cell cultures of various types, including cell cultures of differentiating pluripotent stem cells (hPSC), e.g., human induced pluripotent stem cells (iPS C) and human embryonic stem cells (EPSC), or hPSC-derived neural stem cells, and fibroblast cultures that have been genetically trans-duced to trans-differentiate into neurons (induced neurons).

In some embodiments a method of distinguishing neurons in a cell culture comprising neurons and glia is provided that comprises contacting the cell culture with a first antibody that binds specifically to CD200 and at least a second antibody that binds specifically to a second protein, where the second protein is selected from the group consisting of HLA-A, HLA-B, HLA-C, (HLA-A,B,C) CD49f, CD151 and CD340 or any combination thereof and detecting cells that are CD200$^+$ cells and also exhibit low to negative expression of one or more of HLA-A, HLA-B, HLA-C, CD49f, CD151 and CD340. In some embodiments the cell culture comprises human induced pluripotent stem cells (hiPSC), human embryonic stem cells (hEPSC), fibroblast cultures, neural stem cells, neuroepithelium, neural rosettes, neural progenitor cells or neural crest cells. In some embodiments the cell culture is derived from a heterogeneous mixture of cells. The cells that are CD200+ may be CD200$^{med}$ and CD200$^{high}$ and not CD200$^{low}$. In some embodiments the cell culture comprises neural rosettes that have not undergone a neural stem cell enriching step. The step of detecting cells may be carried out by means of a flow cytometer. In some embodiments the first and second antibodies are detectably and discriminably labeled by direct conjugation with a fluorophore such as fluorescein isothiocynate, allophycocyanin, peridinin chlorophyll protein, phycoerythrin, cyanine 5 or BV421. Neurons may be isolated or enriched by isolating or enriching the population of cells that are CD200$^{med}$ or CD200$^{high}$ cells and also HLA-A,B,C⁻, CD49f⁻, CD151⁻ or CD340⁻. In some embodiments the method of enriching the content of neurons in a cell culture comprises inducing neural differentiation in a cell culture to form neurons and glia, contacting the cell culture with a first antibody that binds specifically to CD200 and at least a second antibody that specifically binds to a second protein, where the second protein is selected from the group consisting of HLA-A, HLA-B, HLA-C, CD49f, CD151 and CD340 any combination thereof and flow cytometrically selecting cells that are CD200+ cells and also negative or low for one or more of HLA-A, HLA-B, HLA-C, CD49f, CD151 and CD340. In some embodiments neuron formation is induced directly from the neural rosettes. In some embodiments the cells that are CD200+ are not CD200$^{low}$. In some embodiments the cell culture does not undergo a neural stem cell enriching step. The first and second antibodies may be detectably and discriminably labeled by direct conjugation with a fluorophore such as fluorescein isothiocynate, allophycocyanin, peridinin chlorophyll protein, phycoerythrin, BV421 or cyanine 5. In some embodiments enriching the content of neurons comprises contacting the cells from a cell culture with antibodies selective for at least one of the group consisting of HLA-A, HLA-B, HLA-C, CD49f, CD151, and CD340 to form an antibody-cell complex wherein the antibodies are attached to a surface that may be attracted or repulsed by a magnetic field and selectively separating the antibody-cell complex from the cell culture by the application of a magnetic field to the cells. The enrichment may be greater than 4 fold.

In some embodiments a cell culture is contacted to a first antibody that binds to CD200, a second antibody binds to HLA-A, HLA-B or HLA-C (i.e., HLA-A,B,C antibody) and the method further comprises contacting the cell culture to a third antibody comprising CD49f, CD151 or CD340 and selecting for cells that are CD200+ and HLA-A,B,C⁻, and also CD49f⁻, CD151⁻ or CD340⁻. In some embodiments a system for the isolation or enrichment of neurons derived from pluripotent stem cells is described comprising a first antibody that specifically binds to CD200, at least a second antibody that specifically binds to a protein selected from the group consisting of HLA-A, HLA-B, HLA-C, CD49f, CD151 and CD340 and combinations thereof, a cell culture comprising neurons and a flow cytometer configured to sort cells that are CD200+ and also one or more of HLA-A⁻, HLA-B⁻, HLA-C⁻, CD49f⁻, CD151⁻ and CD340⁻. The first and second antibodies may be fluorescently labeled antibodies. In some embodiments the second antibody may be a magnetically labeled antibody.

In one embodiment, the cell-surface marker signature that is used to identify neurons in neural differentiation cultures is the high expression of CD 200 such as CD200++ or CD200$^{high}$ which are used interchangeably herein to indicate cells that are CD200+ cells and have a higher than average CD200 signal. In other embodiments cells may be selected by the exclusion of low expression of CD200 (CD200$^{low}$) cells. In some embodiments, the cell-surface marker signature that is used to identify neurons is HLA-A⁻/HLA-B⁻/HLA-C⁻/CD 151⁻/CD49f⁻/CD340⁻/CD200+. In some embodiments a system for the identification of neurons in a population of cells is described that comprises a first antibody that specifically binds to CD200, a second antibody that specifically binds to least one of a group of proteins comprising HLA-A, HLA-B and HLA-C, a third antibody that specifically binds to least one of a group of proteins comprising CD49f, CD151 and CD340, a cell sample and a flow cytometer configured to identify cells that are CD200+ and HLA-A,B,C⁻, and also CD49f⁻, CD151⁻ or CD340⁻.

DETAILED DESCRIPTION

The inventors disclose methods and systems that provide for the isolation and purification of neurons derived directly from any heterogeneous cell population such as cultures containing neural rosettes. The neural rosettes may be derived from stem cell populations such as induced pluripotent stem cells (hiPSC), embryonic stem cells (hEPSC), or fibroblast cultures.

The methods and systems are based on the expression profiles of various cell adhesion molecules that were examined in pluripotent stem cells, neural rosettes, epithelium and neurons. Of the molecules investigated, it is demonstrated that one or more of HLA-A, HLA-B, HLA-C, CD49f, CD340 or CD151 may be negatively selected for in combination with the positive selection of CD200 to identify, isolate or enrich a population of neurons from a cell culture. Certain changes in the expression of one or more these molecules may correlate with the progression of cells from a non-lineage committed cell to a cell committed to a neural lineage. In some embodiments one or more antibodies for these molecules HLA-A, HLA-B, HLA-C, CD49f, CD340 or CD151 in combination with antibodies for CD200 provides for the identification, isolation and/or enrichment of neurons from neural differentiation cultures of pluripotent stem cells. Antibodies for HLA-A, HLA-B, and HLA-C may be a single antibody that selectively binds all three proteins, known collectively as HLA-A,B,C.

Definitions and other information, including protocols and reagents, that are known in the art and that may be useful to understand and practice the present invention are provided in the references cited throughout, in particular, Yuan et al., "Cell-Surface Marker Signatures For The Isolation of Neural Stem Cells, Glia and Neurons Derived from Human Pluripotent Stem Cells." PLoS One. 2011 Mar. 2; 6(3):e17540 where FACS and image based immunophenotyping analysis using antibodies to cell surface markers on naive human embryonic stem cells (hESC) identified prospective cell surface signatures for the isolation of glia and neurons from isolated neural stem cells.

Figure 1:
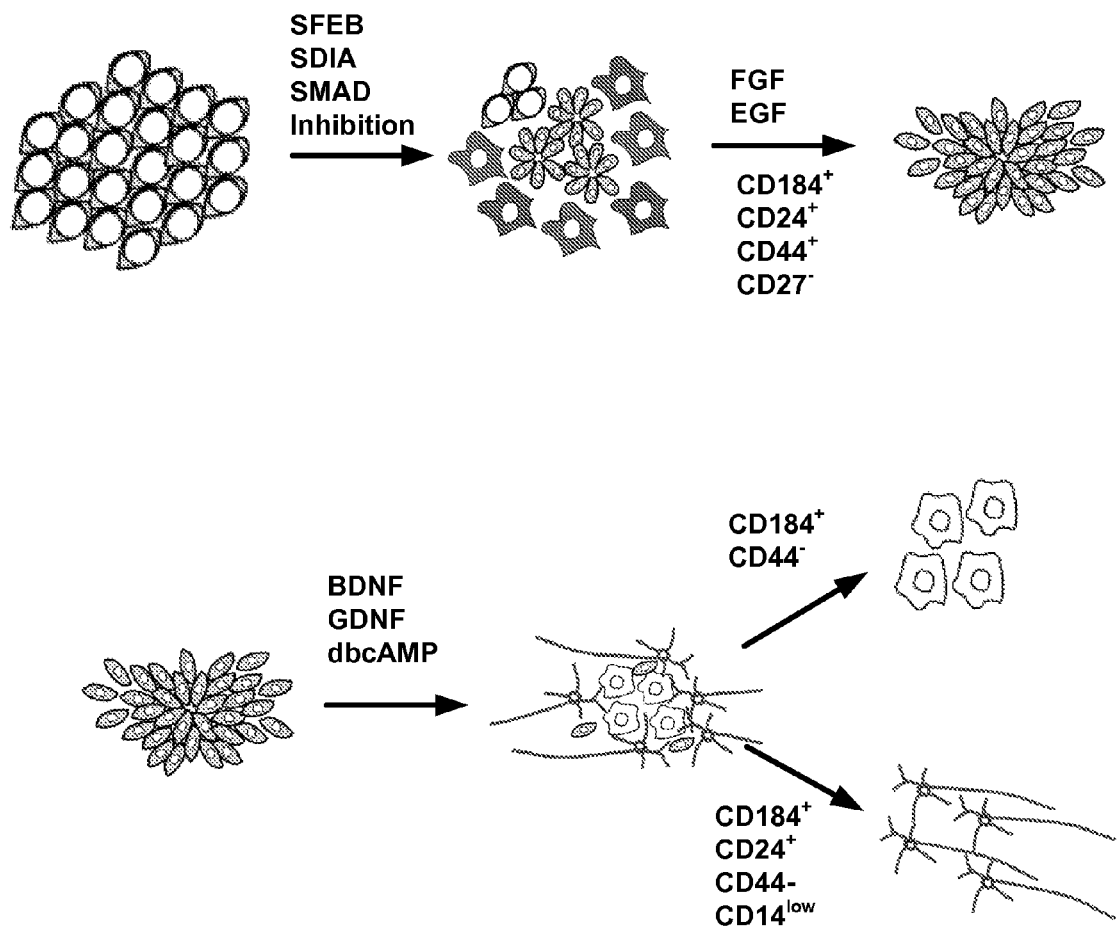
FIG. 1 depicts a prior art cell sorting method for the enrichment of glia and neurons.

FIG. 1 depicts a schematic representation of prior art methods for the induction and isolation of neurons from stem cells described in Yuan et al. Populations of naive human embryonic stem cells (hESC) are cultured and treated to induce neural rosette formation by treatment with SMAD inhibitor (e.g., SB431542, Noggin). Neural stem cells are then isolated from these cells either manually or flow cytometric ally with a set of markers for the identification and isolation of neural stem cells (NSC) in a growth media. Sorted NSC are propagated for many passages and differentiated into mixed cultures of neurons and glia after treatment with a neuron differentiation medium comprising brain-derived neurotrophic factor (BDNF) and glial-cell derived neurotrophic factor (GNDF). A population of neurons that was $CD184^+/CD44^-/CD15^{LOW}/CD24^+$ and a population of glia that was $CD184^+/CD44^+$ were subsequently purified from cultures derived from isolated NSC.

Figure 2:
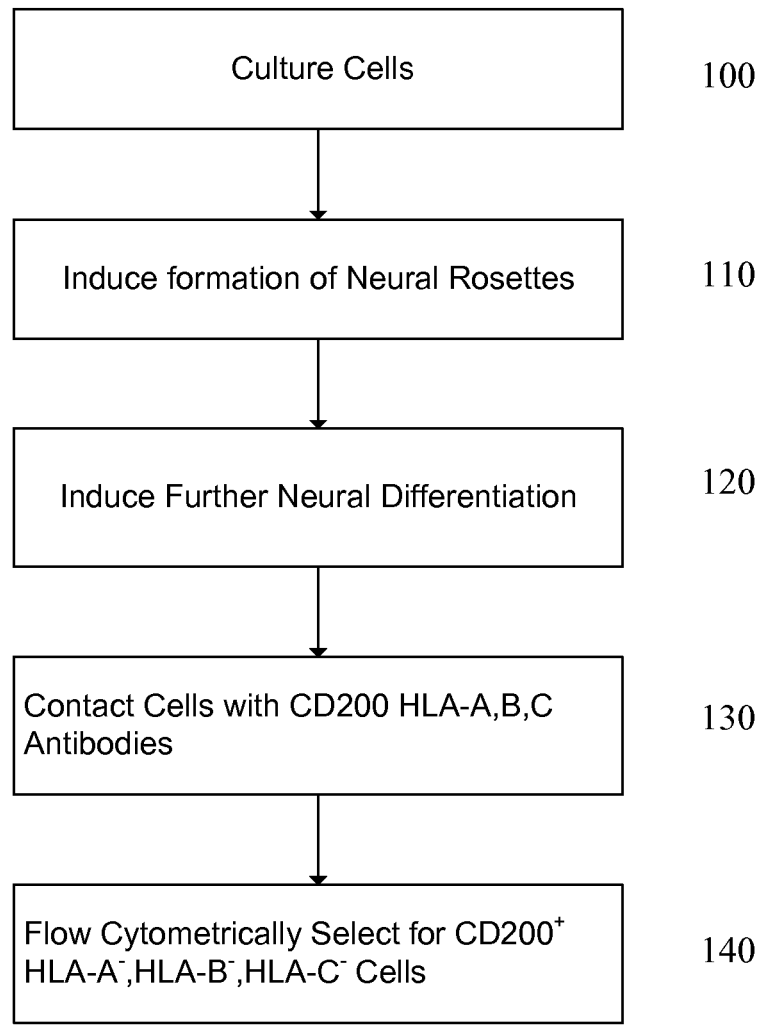
FIG. 2 shows a flow chart depicting steps in an embodiment of this invention.

FIG. 2 shows the steps in an embodiment of this invention wherein neural progenitors committed to forming neurons may be identified and isolated using flow cytometric methods and without the purification or isolation of neural stem cells. Aspects of this invention include the culturing of cells that are capable of neural differentiation (e.g., pluripotent stem cells (hiPSC), human embryonic stem cells (hEPSC), or fibroblast cultures) 100. These cells may be induced to form neuroepithelium, including neural rosettes by any means known in the art, such as treatment with a SMAD inhibitor(s), stromal derived induction activity, or serum free embroid body methods 110. Neuroepithelium formed by this or other methods may be further treated to induce further differentiation into neurons, glia, astrocytes etc. Treatment to induce neuron differentiation from this heterogeneous mixture 120 may include incubation in a medium comprising BDNF, GDNF and adenosine monophosphate (AMP), epithelial growth factor (EGF), fibroblast growth factor (FGF). Cells such as neurons may be identified and/or isolated by the contact with antibodies to selected markers such as CD200, HLA-A, HLA-B, HLA-C, CD49f, CD151, CD340, or any combination thereof 130. The cells may be selected or isolated by flow cytometric assays 140.

Biological markers useful in the present methods are, in general, those that are informative of the state of the neural development system in response to the induction of neural differentiation and may advantageously be used with cell cultures derived from a heterogeneous cell population. Biological markers that are informative of the state of the neuron development pathway, by way of example and not of limitation, include cell-surface proteins such as CD200, HLA-A, HLA-B, HLA-C, CD49f, CD151 and CD340. Biological markers also include RNA and DNA molecules that encode or are otherwise indicative of the aforementioned protein markers. In some embodiments neurons in a cell culture may be identified by the detection of the presence of CD200 in the sample, for example by the contact with fluorescently labeled antibodies that specifically bind to CD200. In certain embodiments, the presence of CD200 is measured in addition to the presence of one or more markers from the group comprising HLA-A, HLA-B, HLA-C, CD49f, CD151 and CD340 and combinations thereof, e.g., HLA-A, HLA-B and/or HLA-C. In some embodiments, neurons are selected for based on cells that are classified as $CD200^+$ cells and also one or more of $HLA-A^-$, $HLA-B^-$, $HLA-C^-$, $CD49f^-$, $CD151^-$ or $CD340^-$. In some embodiments, cells that are $CD200^+$ cells and also one or more of $HLA-A^-$, $HLA-B^-$, $HLA-C^-$, $CD49f^-$, $CD151^-$ or $CD340^-$ are selected for, where $CD200^+$ are cells may be classified as $CD200^+$ and $CD200^{high}$, excluding cells that are $CD200^{low}$. In some embodiments neurons may be identified by contacting a cell culture with a first antibody that binds specifically to CD200 and at least a second antibody that specifically binds to a protein selected from the group consisting of HLA-A, HLA-B or HLA-C, and at least a third antibody that binds specifically to or a protein selected from the group consisting of CD49f, CD151 or CD340; and detecting cells that are $CD200^+$ cells and also one or more of $HLA-A^-$, $HLA-B^-$, $HLA-C^-$ and also $CD49f^-$, $CD151^-$ or $CD340^-$. Neurons may also be detected by selecting for cells that are $CD200^+$ cells and have detectable but low expression of one or more of HLA-A, HLA-B, HLA-C, CD49f, CD151 or CD340.

In some instances, cells in a sample are identified by the expression level of one or more proteins on the cell surface (e.g., in some cases, $CD200^+$ cells in a sample are identified) by detecting the staining intensity of cells stained with a probe (e.g., antibody) that is specific for a cell surface protein of interest (e.g., CD200, HLA-A, HLA-B, HLA-C, CD49f, CD151, CD340, etc.). It will be understood by those of ordinary skill in the art that the stated expression levels reflect detectable amounts of the marker protein on the cell surface. A cell that is negative for staining (e.g., $CD200^-$) (the level of binding of a marker specific reagent is not detectably different from an isotype matched control) may still express minor amounts of the marker and/or there may exist a minor amount of staining intensity not due to the presence of protein (e.g., "background" staining). And while it is commonplace in the art to refer to cells as "positive" (+) or "negative" (−) for a particular marker, actual expression levels are quantitative traits. The number of molecules on the cell surface can vary by several logs, yet still be characterized as "positive". For example, the term "$CD200^+$" as used herein can encompass the terms $CD200^{med}$ and $CD200^{high}$, but does not encompass the term $CD200^{low}$ or $CD200^-$.

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained (i.e., "negative") cells. When displayed in this manner, it is clear that the cells falling in the highest log of staining intensity are "positive" ("high"), while those in the lowest intensity are "negative" or "low". The "low" positively stained cells have a level of staining brighter than that of an isotype matched control, but it is not as intense as brighter stained cells normally found in the population. From lowest intensity to brightest intensity, cells can be "negative", "low", "med" (i.e., medium), or "high". Cells that are "med" or "high" are considered "positive." In some cases, "++" is used to indicate "high" while "+" is used to indicate "med" but both intensity levels are considered to be "positive."

An alternative control may utilize a substrate or substrates having defined densities and/or intensities of a marker on the surface, for example a fabricated bead or cell line, which provides the positive control for one or more levels of intensity.

Measurement of biological markers may be carried out by any conventional technique. Measurements of biological marker molecules may include, for example, measurements that indicate the presence, concentration, expression level, or any other value associated with a marker molecule. Various spectroscopic techniques are available for measuring biological marker molecules, including UV, visible, and infrared spectroscopies. Fluorescent labels, radioactive labels, or other readily identifiable and quantifiable labels may be used to aid in measurement of marker molecules. The expression levels of cell-bound markers may be measured by flow cytometric techniques. Cell surface marker expression has been described for the identification and isolation of many neural cell types by imaging techniques such as fluorescent activated cell sorting (FACS) from embryonic and adult tissue from multiple species. In preferred embodiments flow cytometry may be used to identify and sort cells using methods of this invention. Flow cytometry is a technique for counting and examining microscopic particles such as cells by suspending them in a stream of fluid and capturing the light that emerges from each cell as it passes through a laser beam. Cell surface molecules often referred to as "cluster of differentiation" (CD) molecules may be exploited in flow cytometry to characterize cell populations. For example, in fluorescence-activated cell sorting, a diagnostic antibody (labeled with a fluorophore) is employed, which binds to a surface molecule (e.g., a CD molecule) present on and characteristic of the cell population in question. Thereafter, the fluorophore (attached to the antibody) is activated by a laser beam and the fluorescence signal detected by the flow cytometer. In this manner, fluorescently labeled antibodies can be used to detect and sort cells displaying a specific CD molecule (or set of CD molecules). Fluorophores for use with this or any other detection method by way of example and not of limitation, include fluorescein isothiocynate, allophycocyanin, peridinin chlorophyll protein, phycoerythrin, and cyanine 5, BB421 or any other fluorophore that may be covalently conjugated to an antibody. Systems of this invention may include a flow cytometer, a detectably labeled antibody specific for CD200, detectably labeled antibody or antibodies specific for one of or any combination of HLA-A, HLA-B or HLA-C, CD49f, CD340 or CD151, and a cell culture comprising neurons, so that one or more of these proteins may be detected. Flow cytometers that are utilized in methods and systems described here may be configured to detect low, medium and high signals from the fluorescently labeled antibodies. The particular antibodies utilized in conjunction with the intensity of the signal may provide for a specific pattern of recognition for identifying neurons derived from a cell culture that may comprise a heterogeneous cell population.

The cell surface markers of this invention are related to known families of proteins. Glycoprotein CD200 is a membrane protein expressed by a broad range of cell types. HLA-A, HLA-B, HLA-C, (interchangeably HLA-A,B,C) are HLA protein molecules that make up the Major Histocompatibility Complex (MHC). MHC is a cell surface molecule encoded by a large gene family in all vertebrates. Antibodies to HLA-A, B,C are antibodies that bind to either HLA-A, HLA-B or HLA-C. MHC molecules mediate interactions of leukocytes, also called white blood cells (WBCs), which are immune cells, with other leukocytes or body cells. Antibodies to CD49f bind to the ITGA6 protein product which is the integrin alpha chain alpha 6. Integrins are integral cell-surface proteins composed of an alpha chain and a beta chain. Antibodies to CD340 bind to a member of the epidermal growth factor (EGF) receptor family of receptor tyrosine kinases. Antibodies to CD151 bind to a cell surface glycoprotein that is known to complex with integrins and other transmembrane 4 superfamily proteins.

Figure 3:
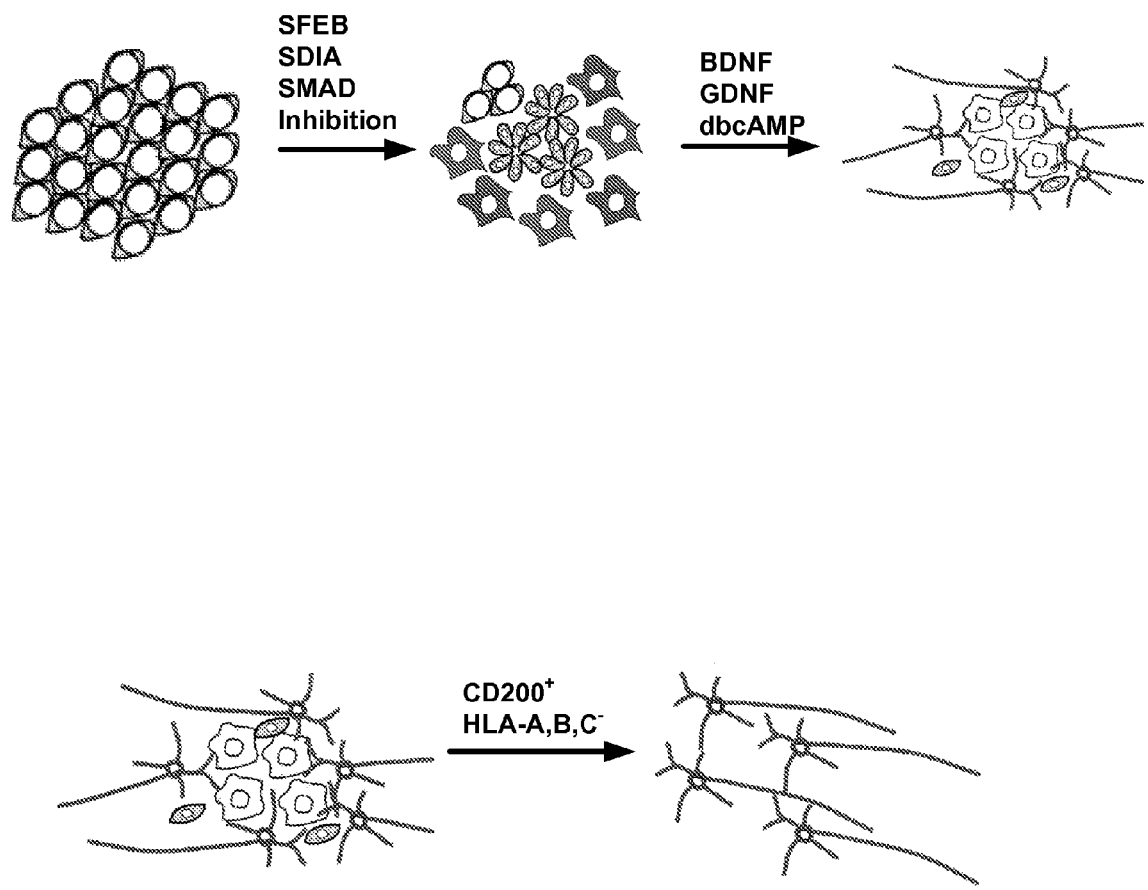
FIG. 3 illustrates an embodiment of the present invention which is a cell sorting method for the enrichment of neurons without the intermediate step of enriching for neural stem cells (NSC).

FIG. 3 schematically illustrates an embodiment of this invention wherein a population of naive human embryonic stem cells (hESC) is induced to form neural rosettes by SMAD inhibition by SFEB in a manner similar to that of Yaun et al. In some embodiments any cell culture that may comprise nueroprogenitors or cells destined to become neurons may be treated with methods and systems of this invention. Cell types that may be combined in methods or systems of this invention include human induced pluripotent stem cells (hiPSC), human embryonic stem cells (hESC), or fibroblast cultures, neural rosettes, neurons and glia. When the cells for induction are neural rosettes as in FIG. 3, the cells may be treated with media that will induce neural differentiation (e.g., BDNF, GDNF and/or dbcAMP) such as the formation of neurons or glia. Media may include reagents such as N2 or B27 or any other reagent or protocol known in the art for inducing neural differentiation. An intermediate step of purification, isolation or separation of neural stem cells is not needed in the methods and systems of this invention. After treatment to induce differentiation, neurons may be identified and/or isolated by contacting the cell culture with antibodies that bind selectively to CD200. In some embodiments neurons may be selected for by contacting the cells with antibodies that selectively bind CD200 and one or more antibodies that selectively bind HLA-A, HLA-B HLA-C, CD49f, CD151, CD340 or any combination thereof. In some embodiments the antibodies are detectably and discriminably labeled by direct conjugation with a fluorophore. The identification may be by any imaging technique that may distinguish a fluorescent signal (e.g., flow cytometry). Cell cultures may be treated with systems of this invention at any time after the induction of neural differentiation such as after 20, 25, 30 or 40 days to insure that neurons are identified and/or isolated. The method beneficially reduces the time to achieving an enriched population on neurons in a cell culture because the step of NSC isolation may be omitted.

Methods and systems of this invention may be used in combination with conventional cell separation techniques to prepare a cell culture enriched in neurons. The enrichment may be based on the selection of cells that are C200$^+$ or CD200$^{high}$ or cells that are CD200$^{med}$ and CD200$^{high}$ (i.e., excluding cells that are CD200$^{low}$). In some embodiments the selection criteria may be based selecting a cell population that is CD200$^+$ or CD200$^{++}$ and also HLA-A,B,C$^-$, CD49f$^-$, CD151$^-$ or CD340$^-$, for example CD200$^{++}$/HLA-A,B,C$^-$. Selection may occur by any means such a via flow cytometric cell sorting. In some embodiments cells that are HLA-A,B, C$^+$, CD49f$^+$, CD151$^+$ or CD340$^+$, may be magnetically sorted out of a cell sample. Magnetic selection may comprise contacting the cell culture with an antibody selective for HLA-A, HLA-B, HLA-C, CD49f, CD151, CD340 or any combination thereof wherein the antibodies are attached to a surface that may be attracted or repulsed by a magnetic field such as magnetic bead. In some embodiments, the antibody specific for the markers of this invention further comprises a magnetic bead such as a ferrous metallic material. Preferably, the magnetic beads are superparamagnetic microparticles, though any type of magnetic bead can be used. The magnetic bead may be attached to the antibody by any means. The magnetic bead may be attached prior to the binding of the antibody to the marker of interest, or subsequent to the formation of the cell-antibody complex. In some instances, the magnetic beads are attached prior to formation of the complex. In embodiments in which the cell-antibody complex has magnetic beads and the antibodies are specific for HLA-A, HLA-B, HLA-C, CD49f, CD151, CD340 or any combination thereof, separation of such a complex from the cell culture comprising neurons preferably comprises contacting the cell culture with a magnetic field such that the cell-antibody complex having the magnetic beads is substantially retained by the magnetic field and the neurons are substantially not retained by the magnetic field. An example of a magnetic field may be magnetized steel wool or a magnetic field in a flow cytometer. The remaining cells may then be selectively sorted for by using antibodies selective for CD200. The invention also includes embodiments in which separation of a cell culture into a first cell population having substantially no cells that are positive for HLA-A, HLA-B, HLA-C, CD49f, CD151, CD340 or any combination thereof and a second cell population having an enriched population for neurons. The second cell population may then be selected for CD200$^+$ or CD200$^{++}$ cells for further enrichment. Methods of this invention may yield enrichment values on the order of 2, 4, 6 or 10 fold.

A system of this invention may comprise a cell culture comprising neurons or neuroprogenitors, an antibody that specifically binds to CD200 and a flow cytometer configured to sort cells that are CD200$^+$. The systems of this invention may also include a second antibody that specifically binds to at least protein from selected from the group proteins consisting of HLA-A, HLA-B, HLA-C, CD49f, CD151 or CD340, where the system may include an antibodies specific for 2 or more of, 3 or more of, 4 or more of, 5 or more of, including all 6 of these proteins (e.g., a system that includes a specific antibody for each of these 6 different proteins) wherein the flow cytometer is configured to sort cells that are CD200$^+$ and on or more of HLA-A,B,C$^-$, CD49f$^-$, CD151$^-$ or CD340$^-$. In some embodiments the systems of this invention may also include a third antibody that specifically binds to least a protein selected from the group of proteins consisting of CD49f, CD151 or CD340 wherein the flow cytometer is configured to sort cells that are CD200$^+$ and HLA-A,B,C$^-$ and on one or more of CD49f$^-$, CD151$^-$ or CD340$^-$. Other systems of this invention include reagents, kits, and assays for the isolation or enrichment of neural cell types from neural differentiation cultures of hPSC and induced neuronal cultures from fibroblasts. Methods and systems of this invention may be used for diagnostic tools for the analysis of neural cell types derived from patient's cells. Enrichment of neural cell types for screening drugs (or small molecule) candidates on neural cell types derived from heterogeneous cell culture compositions such as neural rosettes, hPSC or patient's cells. The following non-limiting examples further illustrate the present invention.

EXAMPLES

Example 1

Cultures of H9hESCs were obtained from WiCell (Madison, Wis.) were expanded cells were then differentiated as follows:

Day 1: Embryoid bodies (EB) were made by treatment with Dispase and placed in knock-out serum replacement (KOSR) media (Standard WiCell hESC media w/o bFGF) containing 10 µm Y-27632 (Rock inhibitor), 2.5 µm Dorsomorphin, 10 µm SB43152. Low adhesion 6 well plates were used and 4 mls of media were added per well.

Day 2: Rock inhibitor was removed and cells changed to KOSR media containing 2.5 µm Dorsomorphin, 10 µm SB43152.

Day 4/5: EBs were plated on matrigel coated plates in ITS media [D-MEM/F-12 w/Glutamax™ (Life Technologies™)+1×ITS (BD™)]+2.5 µm Dorsomorphin+10 µm SB43152. 4 mls of the EBs are plated in the wells and 10 mls of ITS media were added into a 10 cm coated plate. EBs were fed every 2-3 days.

Day 10/11: Cell media was changed to ITS.

Day 15/18$^+$: Media was changed to ITS media+20 ng/ml FGF for 24-48 hrs. Cell death and neuron differentiation were observed.

Day 18/20: Life Technologies StemPro® EZPassage™ passaging tool was used to cut squares into culture. The squares were scraped and pelleted. One 10 cm of culture was plated into two T150 flasks that were coated with Poly-ornithine and Laminin in D-MEM/F-12 w/Glutamax™ media. The media also contained 1 µm dbcAMP+10 ng/ml BDNF+ 10 ng/ml GDNF.

Figure 4:
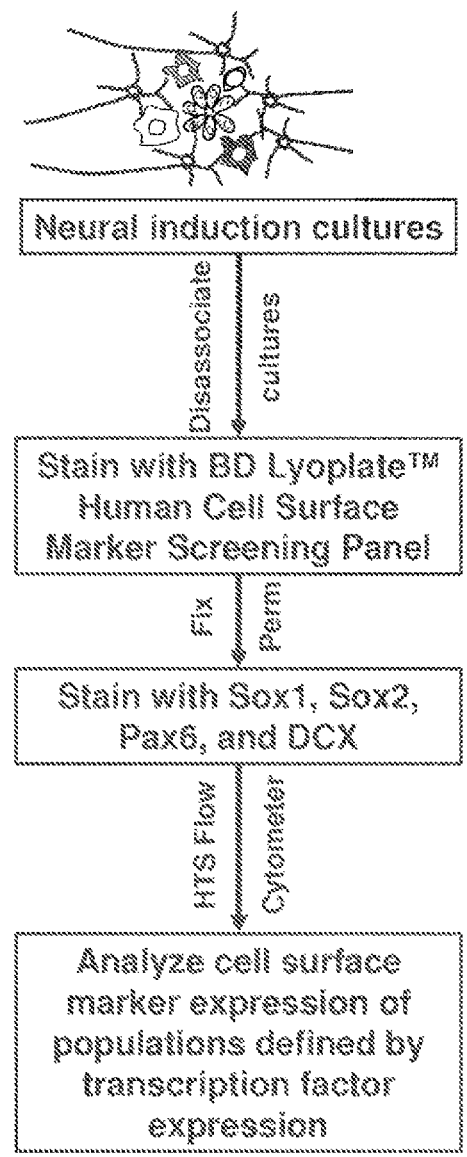
FIG. 4 depicts a flow chart showing the immunophenotyping screening approach used to identify a cell surface signature for isolating neurons derived from differentiating pluripotent stem cell cultures.
Figure 5:
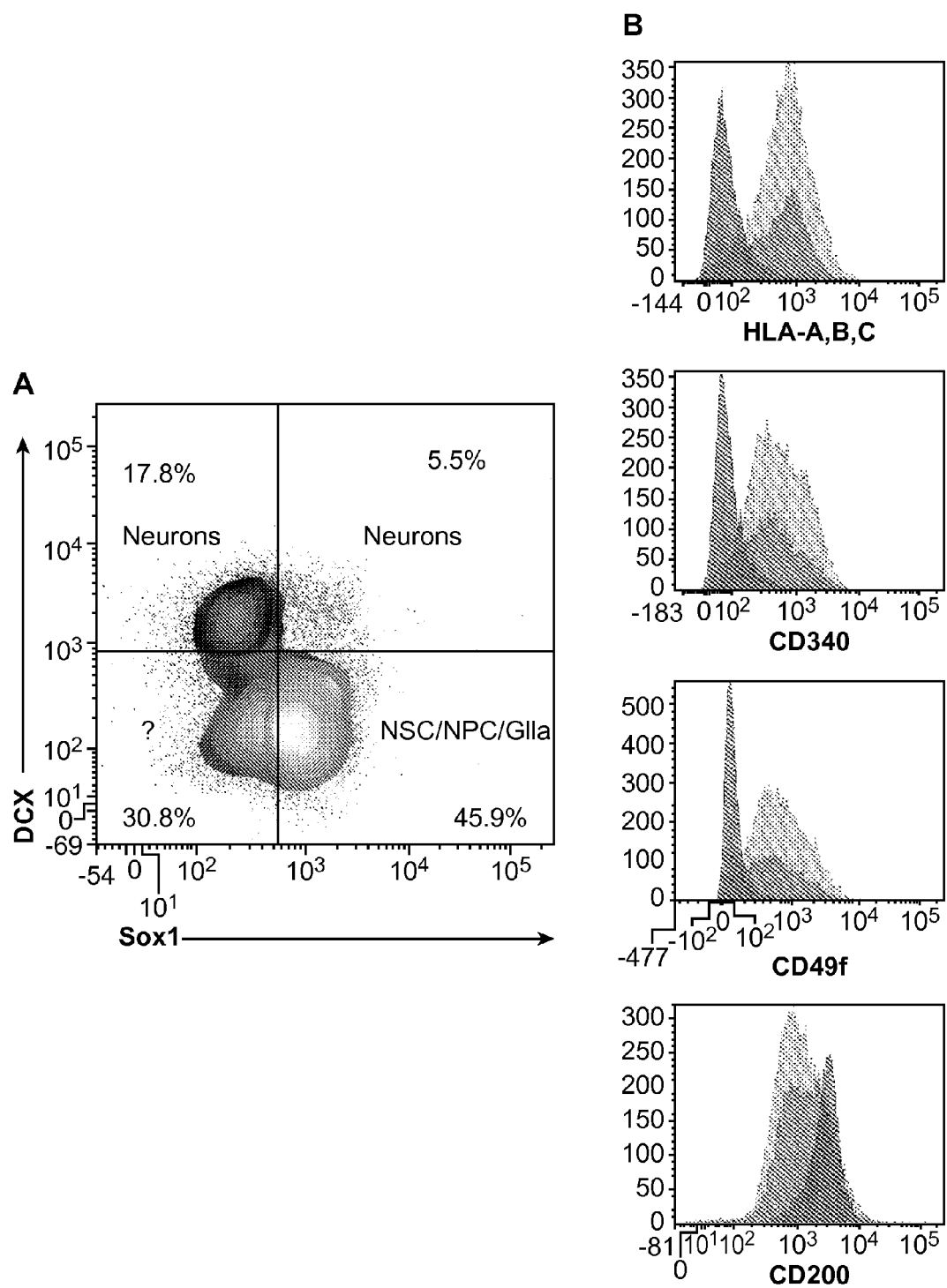
FIG. 5, Panels A and B depict the fluorescence profiles of intracellular markers and candidate cell surface markers identified in the screen the screening approach of FIG. 4.

Day 40: The cultures were sorted analyzed and analyzed. FIG. 4 describes the neuron isolation immunophenotype discovery workflow utilized here. Neural induction cultures were stained with BD Lyoplate™ Human Cell Surface Marker Screening Panel to screen for surface markers and then subsequently stained with SOX1, SOX2, PAX6 and DCX to screen for neurons using intracellular markers. Finally, the cell surface marker expression population was analyzed to determine novel cell surface markers for neurons from a heterogeneous population of cells. The 2D plot (FIG. 5A) shows the DCX$^+$Sox1$^-$ and DCX$^+$Sox1$^+$ population identified as neurons. The differentiation cultures were analyzed to be able to isolate/enrich the neurons. The four histograms shown in FIG. 5B show a sampling of various markers identified in the screen that are differentially expressed on the neurons as compared to the other populations.

Figure 6:
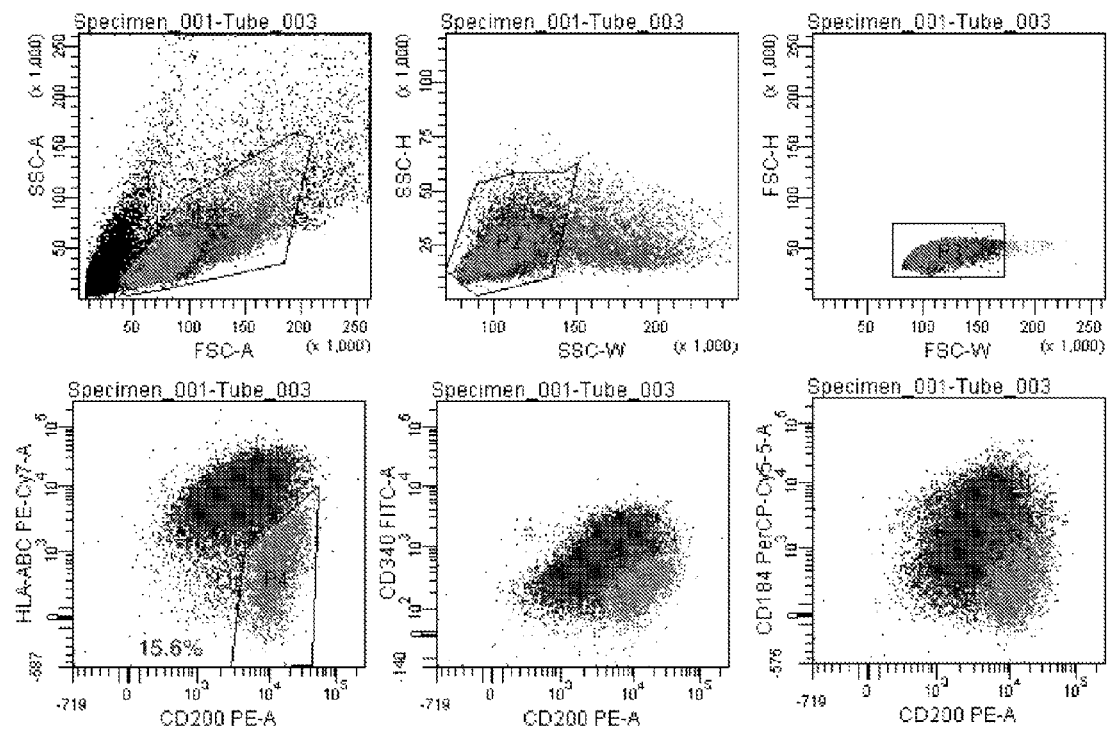
FIG. 6 illustrates the gating strategy used for the identification of neurons for cell sorting.

The neurons were sorted with a 100 µm nozzle at approximately 20 psi. Cells were stained in basal media and collected in basal media. FIG. 6 shows the gating strategy used sort neurons from the neural induction cultures. The neural gate was identified as follows, clock wise from the upper left hand side: cells based on light scatter, P2+P3− single cells based on light scatter and P4 are identified as neurons based on CD200 and HLA-A,B,C expression. There are also 2 additional plots showing the expression CD340 and CD184 of the cells in the neuron gate P4 (CD200++/HLA-B−, HLA-C−).

Figure 7:
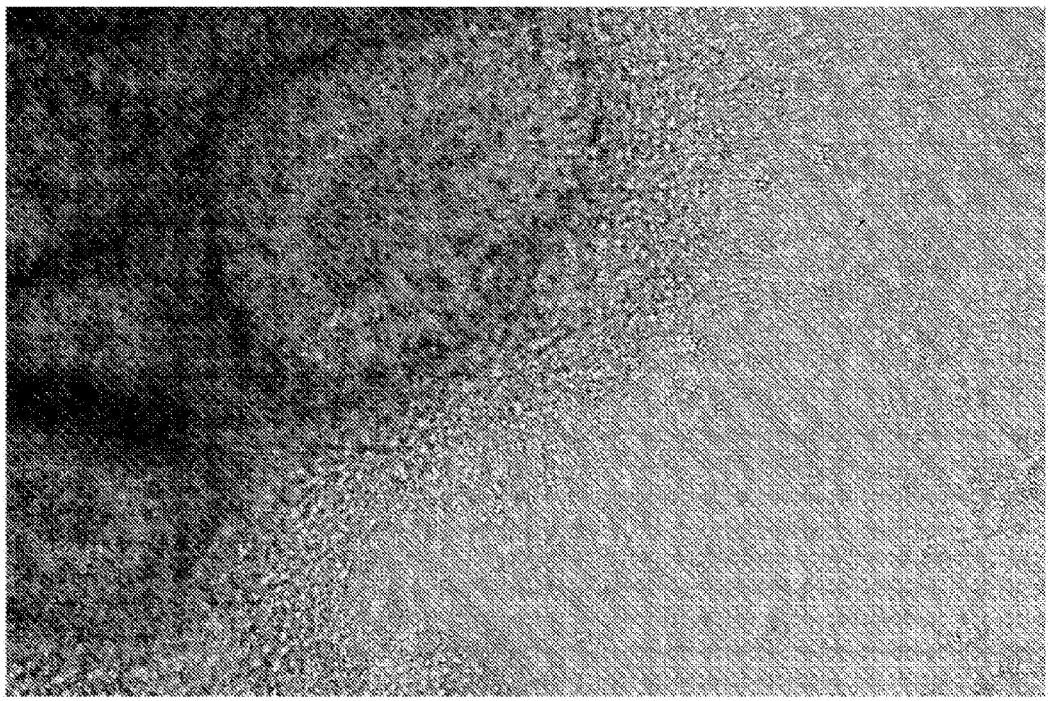
FIG. 7 shows an image of a neural differentiation culture prior to sorting, illustrating the heterogeneity of the cell culture.
Figure 8:
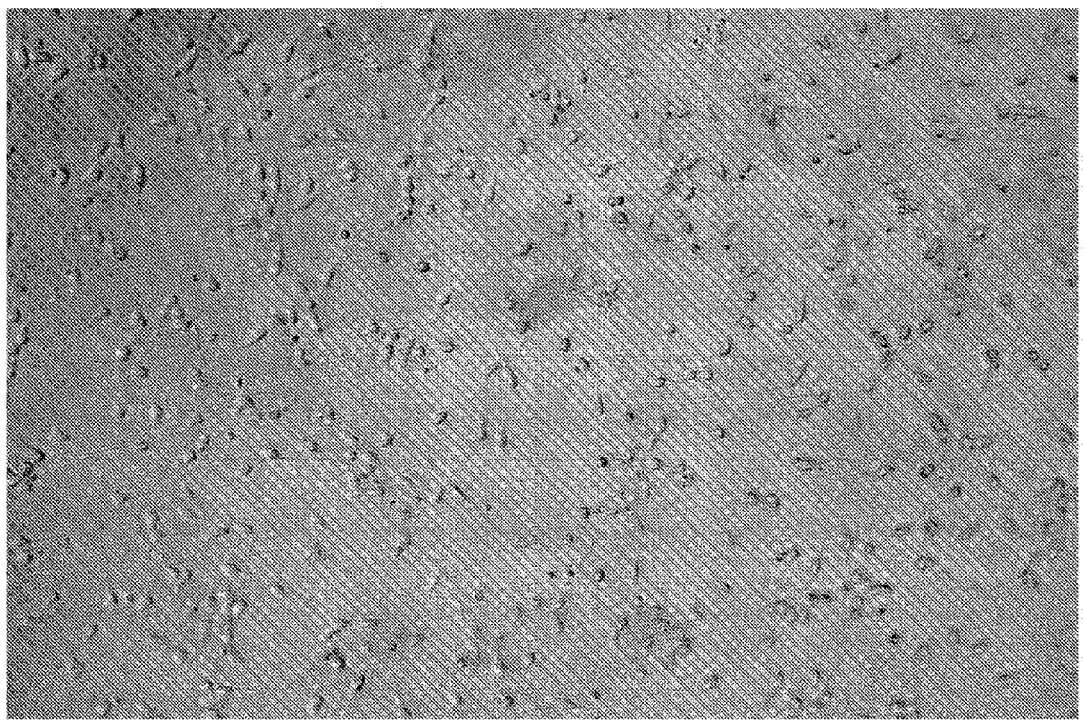
FIG. 8 shows an image of neurons sorted from a heterogeneous cell culture using the cell-surface marker signature of the present invention.

FIGS. 7 and 8 show a light microscope image of pre-sort and two days post-sort cultures. Neurons imaged in the post-sort image are qualitatively very pure based on appearance. Round donut-like structures observed in FIG. 7 are neuroepithelium containing NSC. Neuronal projections are identified emanating from the neural colonies.

Figure 9:
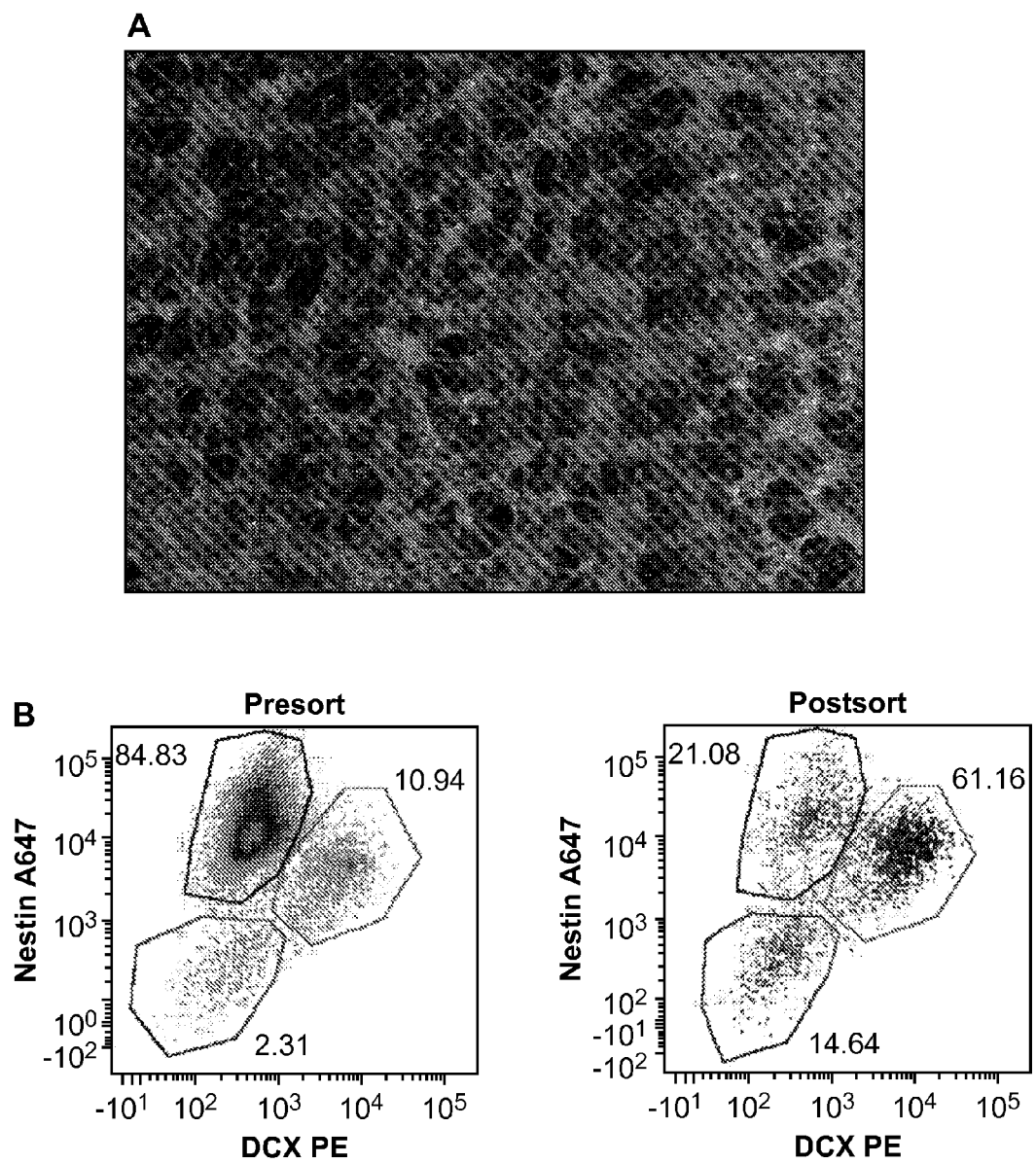
FIG. 9A, shows an image of sorted neurons stained for the neuronal marker betaIII-tubulin and the NSC marker Nestin, which shows that the cells are highly pure.
FIG. 9B, shows the semi-quantitative flow analysis of sorted neuronal cultures before and after sorting.

FIG. 9A shows a fluorescence microscopy image of sorted CD200++/HLA-B−, HLA-C−, 7 days after sort. The cells were sorted and plated in 96 well imaging plates at ~50,000 cells/well and cultured for 7 days in D-MEM/F-12 w/Glutamax™ media containing 1×N2 and 1×B27. Neurons are identified by beta tubulin staining, contaminating "non-neurons" are identified by Nestin staining and all cell nuclei identified by DAPI staining.

The 2D plots shown in FIG. 9B illustrate the analysis of the neural cell cultures immediately before cell sorting and immediately after cell sorting. The upper left gate consists of "non-neurons" as seen by the Nestin++/DCX− staining. The gate on the upper right consists of neurons as seen by the Nestin+/DCX+ staining. The plots indicate that the sorted neuronal cultures are about 60% pure.

Example 2

Figure 10:
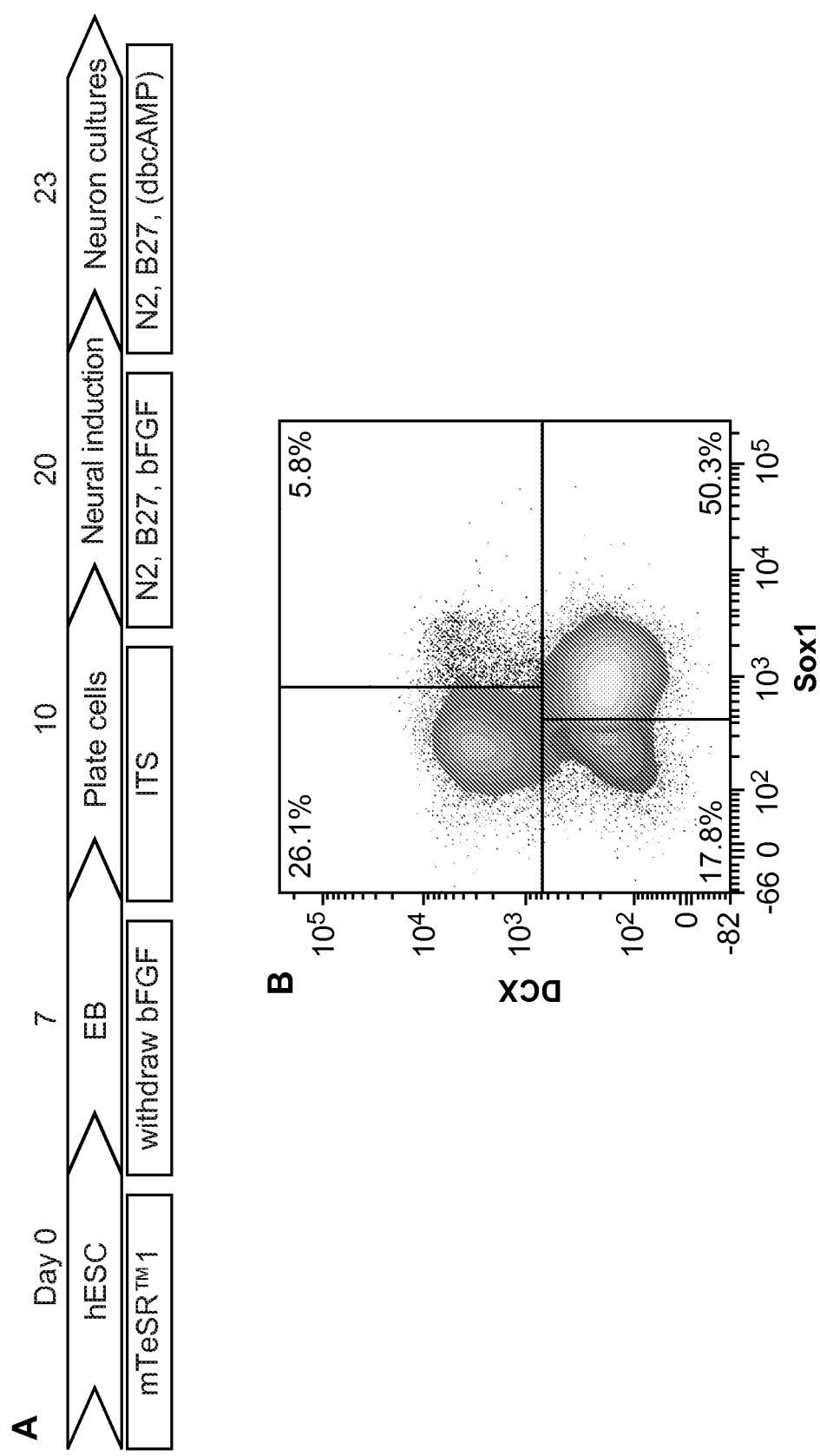
FIG. 10, Panels A, B, C, and D show a series of 2D plots and histograms generated during flow cytometric analysis of differentiated neurons.
Figure 10:
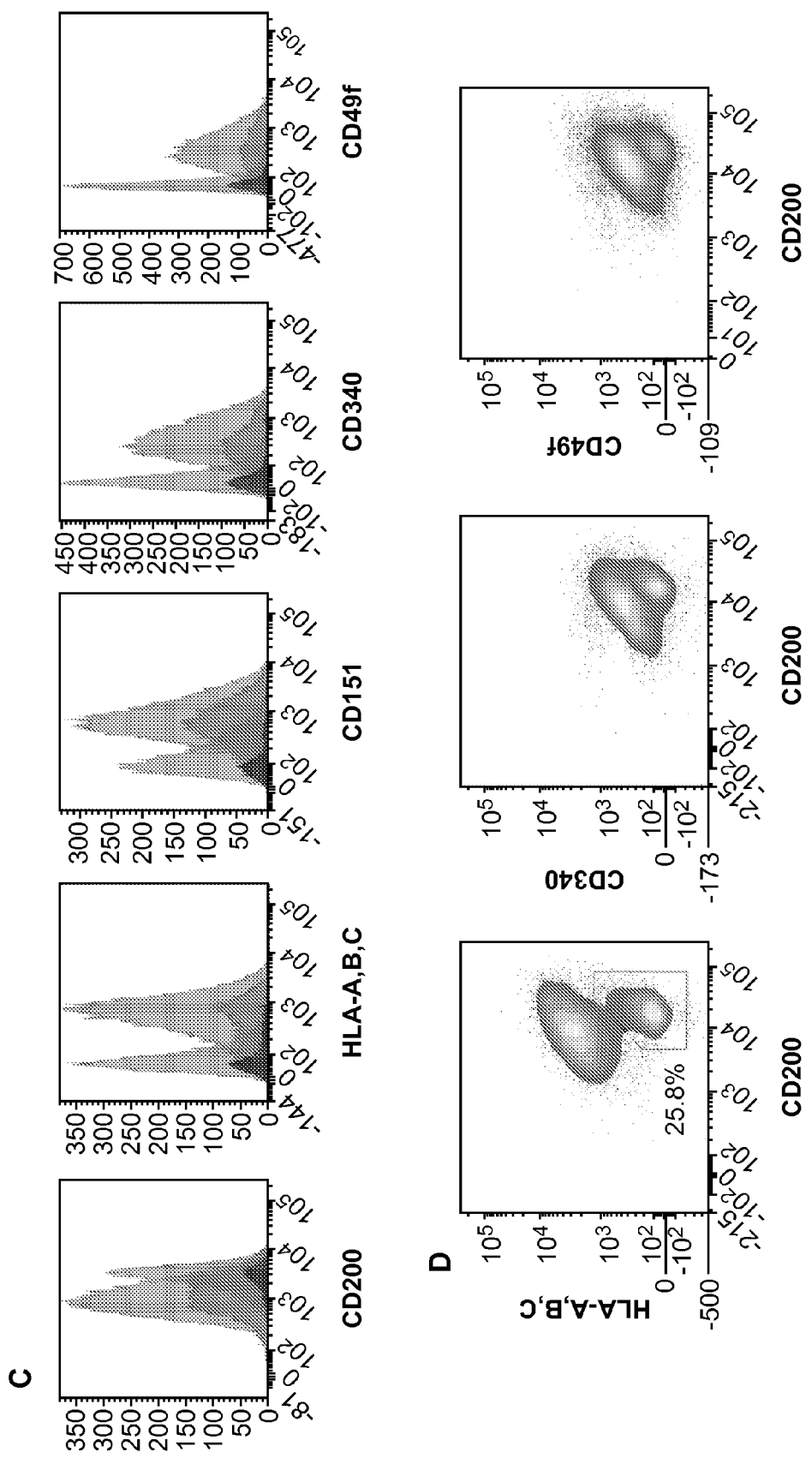

FIG. 10A shows an outline of the cell culture and differentiation process. H9hESCs were cultured and expanded from cells obtained from WiCell (Madison, Wis.). They were then differentiated as follows:

Day 7: Embryoid bodies (EBs) were made with Dispase and placed in KOSR media (Standard WiCell hESC media w/o bFGF) containing 10 μm Y-27632 (Rock inhibitor), 2.5 μm Dorsomorphin, and 10 μm SB43152. Low adhesion 6 well plates were used and 4 mls media were added per well.

Day 8: Rock inhibitor was removed and the media was changed to KOSR media containing 2.5 μm Dorsomorphin, 10 μm SB43152.

Day 10/11: EBs were plated on matrigel coated plates in ITS media [D-MEM/F-12 w/Glutamax™ (Life Technologies 105655018)+1×ITS (BDcat no 354351)]+2.5 μm Dorsomorphin+10 μm SB43152. 4 mls the EBs were plated in the wells and 10 mls of ITS media were added into a 10 cm coated plate. EBs were fed every 2-3 days.

Day 15/11: Cell media was changed to ITS.

Day 20/23: The media was changed ITS media+20 ng/ml FGF for 24-48 hrs. Cell death and neuron differentiation is observed.

Day 23/25: Using Life Technologies StemPro® EZPassage™ passaging tool, squares were cut into culture. One 10 cm of culture was plated into two T150 flasks that were coated with Poly-ornithine and Laminin in D-MEM/F-12 w/Glutamax™ media containing 1×N2 and 1×B27 along with 1 μm dbcAMP+10 ng/ml BDNF+10 ng/ml GDNF.

Day 45: The cultures were sorted analyzed and analyzed.

Neural induction cultures were stained with DCX and Sox1 to provide intracellular controls for neuron differentiation. FIG. 10B shows the 2D plot illustrating the gating strategy. DCX+Sox1− and DCX+Sox1+ population were defined as neurons. Overlaid histograms of markers that were identified in the screen are shown in FIG. 10C. CD200 was identified as a positive marker for neurons. HLA-A, HLA-B, HLA-C, CD151, CD340 and CD49f were identified as negative markers of contaminating cells in the culture. The differential expression of these markers may allow for the isolation of neurons. Results of co-staining of CD200 with HLA-A, HLA-B, HLA-C or CD340 or CD49f to identify a combination of markers for sorting are shown on 2D plots in FIG. 10D.

Figure 11:
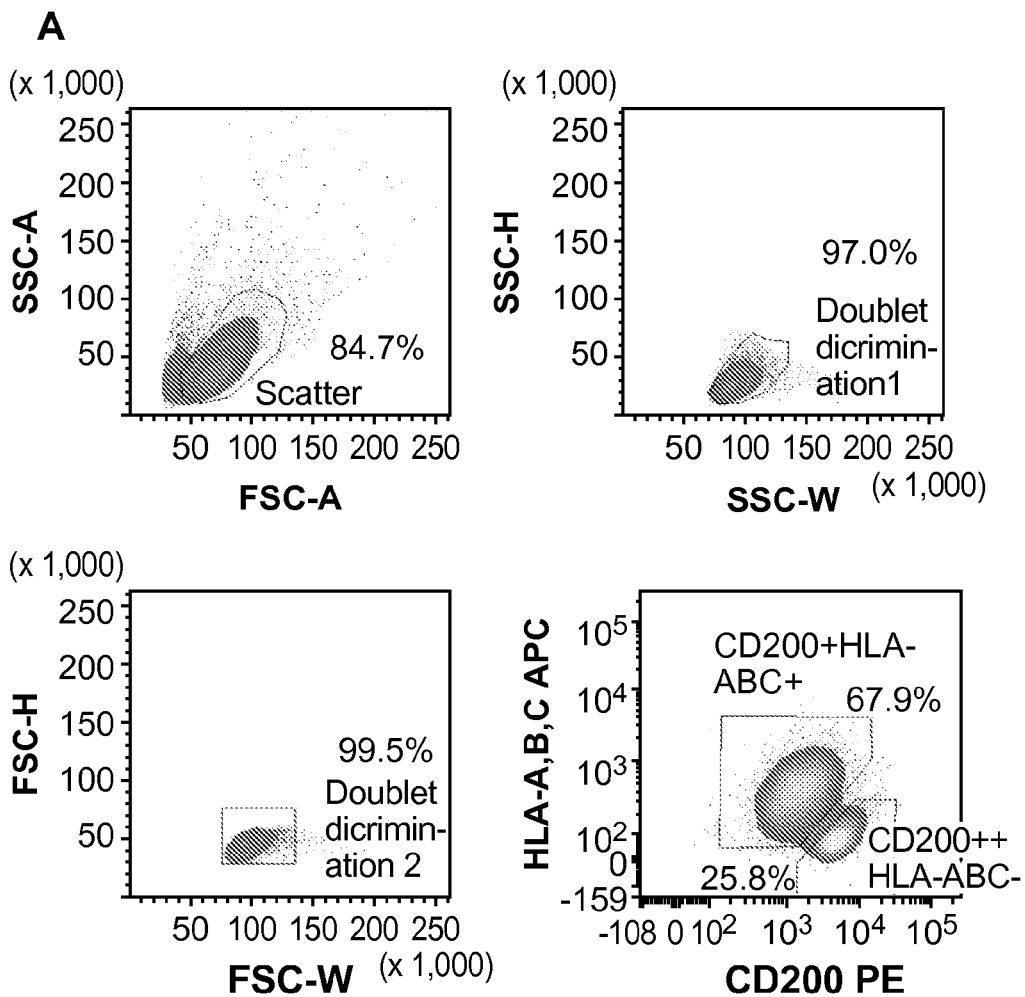
FIG. 11, Panels A, B, C, and D show a series of 2D plots generated during flow cytometric analysis of differentiated neurons before and after fluorescence activated cell sorting.
Figure 11:
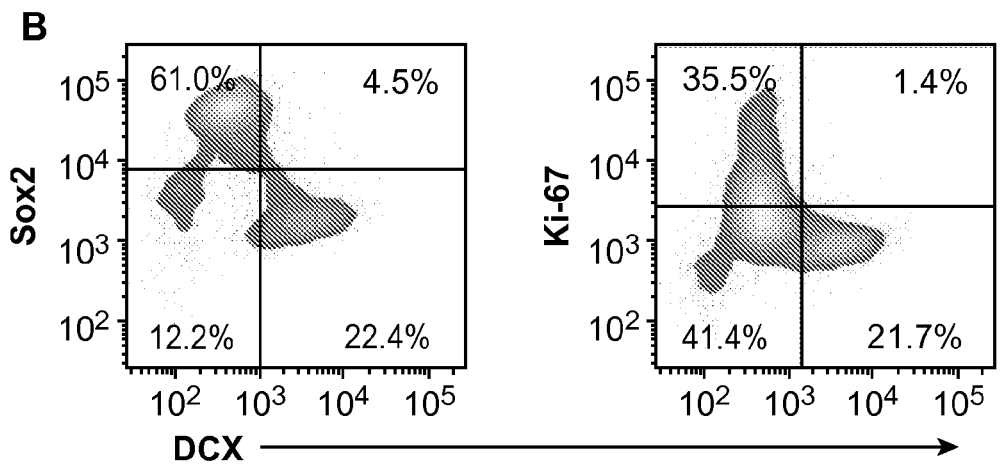
Figure 11:
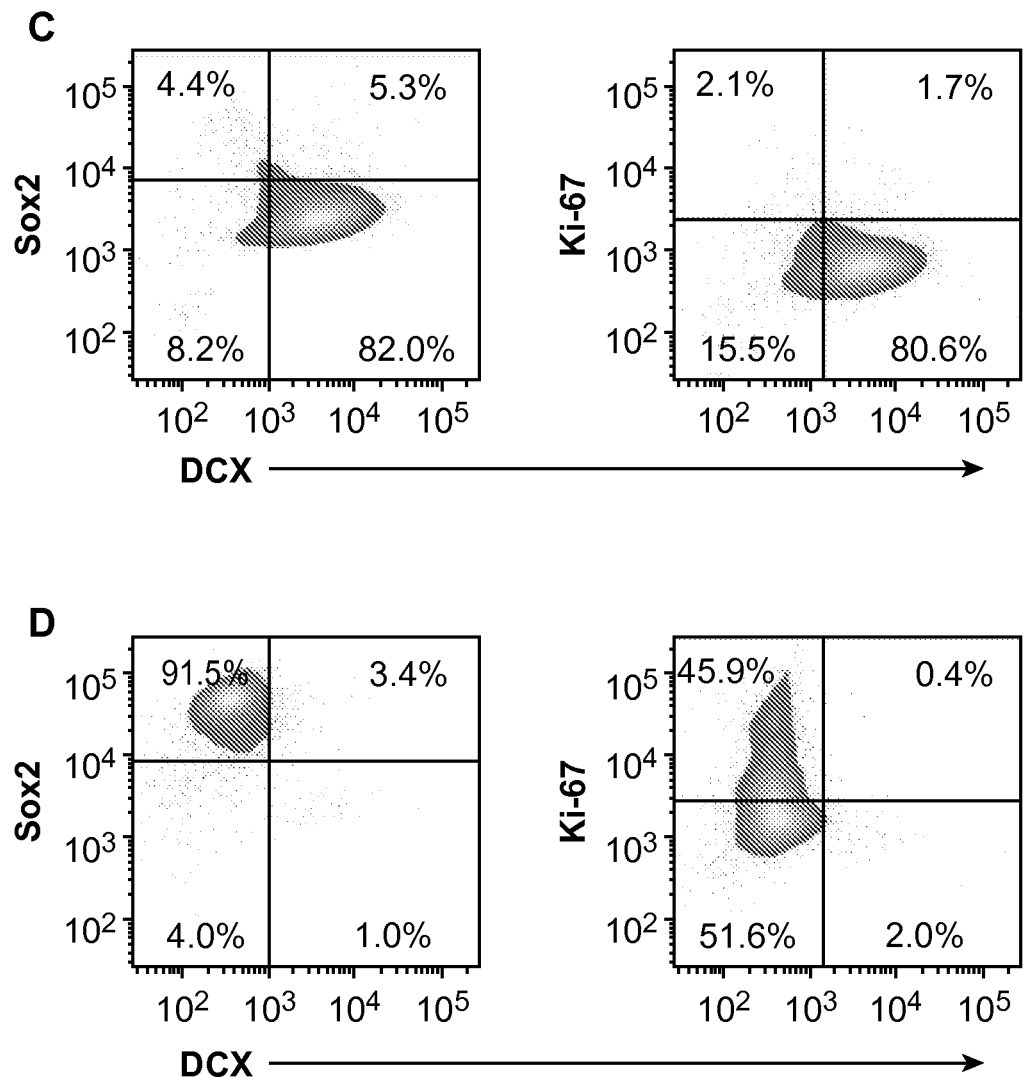

FIGS. 11A-D show results of the gating analysis used to sort neurons from the neural induction cultures. Plots depicted FIG. 11A show scatter discrimination used to sort cells based on light scatter to account for doublet discrimination insure that single cells based on light scatter are analyzed. CD200++/HLA-A−/HLA-B−/HLA-C− plots are used to identify neurons based on CD200 and HLA-A, HLA-B or HLA-C expression and confirmed using DCX/SOX2/Ki67 analysis. FIG. 11B depicts the flow analysis of neural culture before sorting. Neurons are identified by the expression of DCX and lack of expression of Sox2 and Ki-67 (DCX+Sox2−ki67−). FIG. 11C depicts the flow analysis of CD200++/HLA-A−/HLA-B−/HLA-C− cells after cell sorting of neural cultures. Neurons are identified by the expression of DCX lack of expression of Sox2 and Ki−67 (DCX+Sox2−ki67). FIG. 11D depicts the flow analysis of CD200+/HLA-A,B,C+ cells after cell sorting of neural cultures. Neurons are identified by the expression of DCX and lack of expression of Sox2 and Ki67 (DCX+/Sox2−/ki67−).

Example 3

Figure 12:
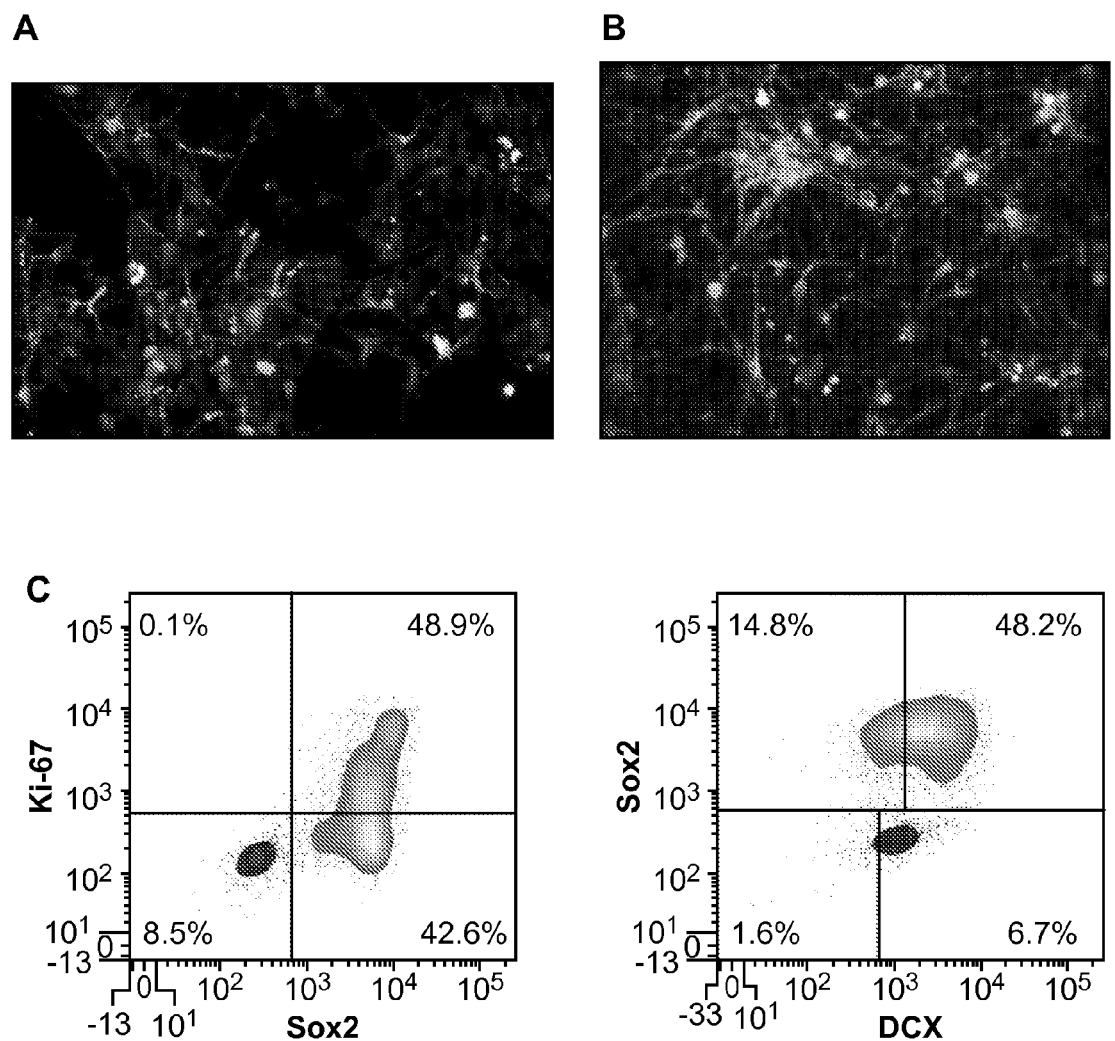
FIG. 12, Panels A, B, C, D, and E show a series of 2D plots and images generated during flow cytometric analysis of differentiated neurons before and after magnetic depletion.
Figure 12:
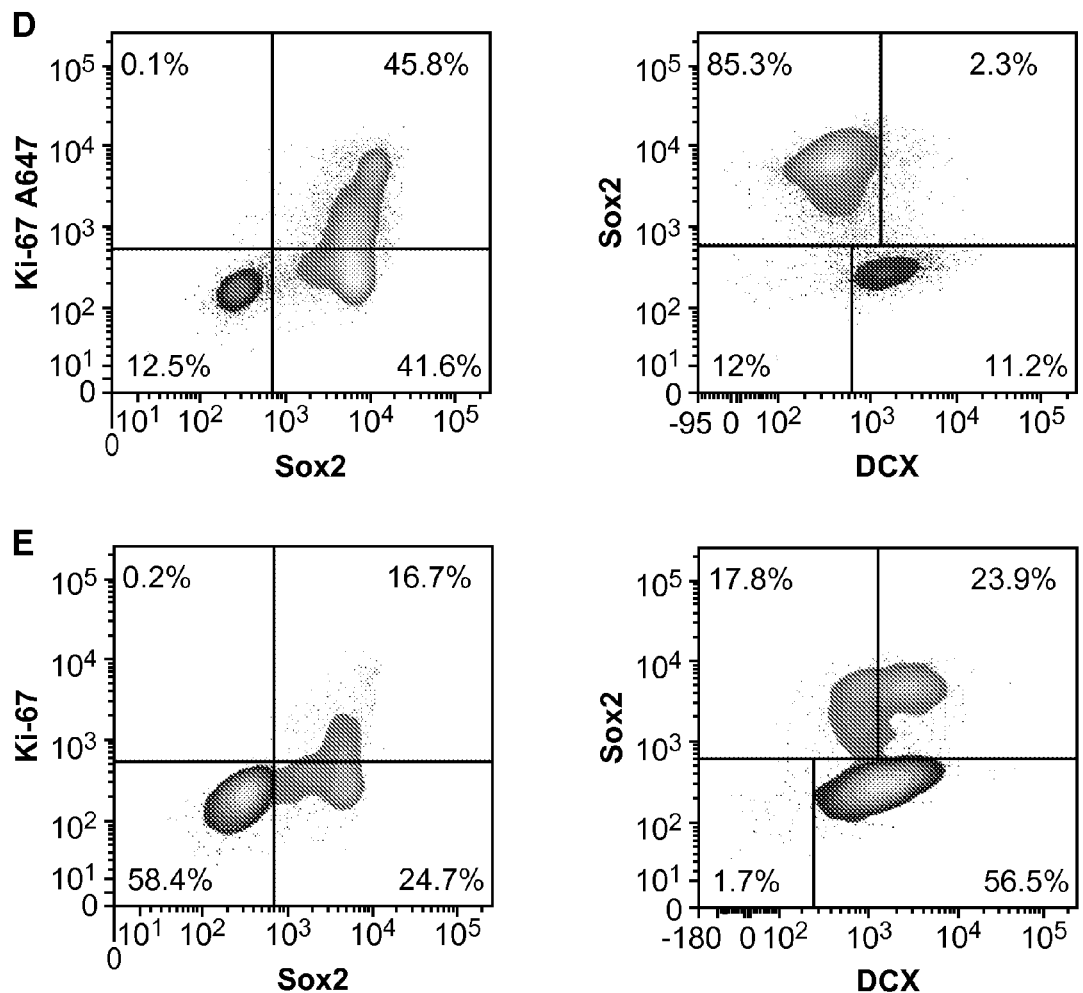

Neuron formation was induced as described above. The cell culture was contacted with the following antibodies; PE CD340, PE HLA-A,B,C and PE CD49f. The cells were then subjected to magnetic depletion. A magnetic nanoparticle conjugated to an antibody that binds PE was used to bind the PE conjugated antibodies that were used on the cell culture. The magnetic nanoparticles were then separated from the cell solution by placing it next to a magnetic field. The enriched and depleted fractions were then analyzed by flow cytometry and image analysis. Image analysis of neural culture before (12A) and after (12B) magnetic depletion is shown in FIGS. 12A and 12B. Neural cultures were disassociated, stained with conjugated antibodies and the plated on 96 well imaging plates and cultured for 7 days. Neurons are identified by the expression of Tuj1 and the lack of expression of Nestin and ki67 (Tuj1+/Nestin−/ki67−). Nuclei are stained with DAPI. Flow analysis of the depleted fraction (FIG. 12C) shows the neuron population which are identified by the expression of DCX and lack of expression of Sox2 and Ki-67. 2-plots of the samples before depletion (12D), and after depletion (12E) are shown. Neurons are identified by the expression of DCX and lack of expression of Sox2 and Ki67 (DCX+/Sox2−/ki67−). Data analysis indicate that depletion of cells in a cell culture comprising neurons with magnetically labeled antibodies specific for PE CD340, PE HLA-A,B,C and PE CD49f will result in an enrichment of neurons in a cell culture.

All patents, patent publications, and other published references mentioned herein are hereby incorporated by reference in their entirety as if each had been individually and specifically incorporated by reference herein. While preferred illustrative embodiments of the present invention are described, it will be apparent to one skilled in the art that various changes and modifications may be made therein without departing from the invention, and it is intended in the appended claims to cover all such changes and modifications which fall within the true spirit and scope of the invention.

What is claimed is:

1. A method of distinguishing neurons from other cells in a cell culture, the method comprising:

contacting the cell culture with a first antibody that specifically binds to CD200 and at least a second antibody that specifically binds to a protein selected from the group consisting of HLA-A, HLA-B, HLA-C, CD49f, CD151 and CD340; and distinguishing cells that are CD200$^+$ cells and also exhibit low to negative expression of one or more of HLA-A, HLA-B, HLA-C, CD49f, CD151 and CD340 from other cells in the cell culture wherein cells that are CD200$^+$ and also exhibit one or more of HLA-A$^-$, HLA-B$^-$, HLA-C$^{-1}$, CD49f$^-$, CD151$^-$ or CD340$^-$ are neurons.

2. The method of claim 1 wherein the cell culture comprises human induced pluripotent stem cells (hiPSC), human embryonic stem cells (hEPSC), neural crest cells, fibroblast cells, neural stem cells or any combination thereof.

3. The method of claim 1 wherein the cell culture is derived from a heterogeneous population of cells.

4. The method of claim 1 wherein the cell culture comprises neural rosettes.

5. The method of claim 1 wherein the cell culture comprises neural epithelium.

6. The method of claim 1 where the CD200$^+$ cells are CD200$^{med}$ and CD200$^{high}$.

7. The method of claim 1 wherein the cell culture has not undergone a neural stem cell enriching step.

8. The method of claim 1 wherein the step of distinguishing cells is carried out by means of a flow cytometer.

9. The method of claim 1 wherein the first and second antibodies are detectably and discriminably labeled by direct conjugation with a fluorophore.

10. The method according to claim 9, wherein the method further comprises identifying cells that are CD200$^+$ cells and also exhibit low to negative expression of one or more of HLA-A, HLA-B, HLA-C, CD49f, CD151 and CD340 as neurons.

11. The method according to claim 10, wherein the cells identified as neurons are HLA-A$^-$/HLA-B$^-$/HLA-C$^-$/CD151$^-$/CD49f$^-$/CD340$^-$/CD200$^+$.

12. The method of claim 1 further comprising enriching the population of cells that are CD200$^{++}$ cells and also exhibit one or more of HLA-A$^-$, HLA-B$^-$, HLA-C$^-$, CD49f$^-$, CD151$^-$ or CD340$^-$.

13. A system for the isolation or enrichment of neurons from a cell culture comprising:
- a first antibody that specifically binds to CD200;
- a second antibody that specifically binds to a protein selected from the group consisting of HLA-A, HLA-B, HLA-C, CD49f, CD151 and CD340;
- a cell culture comprising neurons; and
- a flow cytometer configured to sort cells that are CD200$^+$ and also exhibit one or more of HLA-A$^-$, HLA-B$^-$, HLA-C$^-$, CD49f$^-$, CD151$^-$ or CD340$^-$.

14. The system of claim 13 wherein the first and second antibodies are fluorescently labeled antibodies.

* * * * *